(12) United States Patent
Graf

(10) Patent No.: US 6,888,919 B2
(45) Date of Patent: May 3, 2005

(54) RADIOTHERAPY APPARATUS EQUIPPED WITH AN ARTICULABLE GANTRY FOR POSITIONING AN IMAGING UNIT

(75) Inventor: Ulrich Martin Graf, Leigrüppenstrasse (CH)

(73) Assignee: Varian Medical Systems, Inc., Palo Alto, CA (US)

( * ) Notice: Subject to any disclaimer, the term of this patent is extended or adjusted under 35 U.S.C. 154(b) by 188 days.

(21) Appl. No.: 10/033,327

(22) Filed: Nov. 2, 2001

(65) Prior Publication Data

US 2004/0024300 A1 Feb. 5, 2004

(51) Int. Cl.$^7$ .................................................. A61N 5/10
(52) U.S. Cl. ......................................... 378/65; 378/197
(58) Field of Search ........................... 378/19, 98.8, 65, 378/195, 196, 197, 198, 9; 250/374

(56) References Cited

U.S. PATENT DOCUMENTS

| | | |
|---|---|---|
| 3,133,227 A | 5/1964 | Brown et al. |
| 3,144,552 A | 8/1964 | Schonberg |
| 3,193,717 A | 7/1965 | Nunan |
| 4,149,247 A | 4/1979 | Pavkovich et al. |
| 4,149,248 A | 4/1979 | Pavkovich et al. |
| 4,208,675 A | 6/1980 | Bajon et al. |
| 4,209,706 A | 6/1980 | Nunan |
| 4,521,808 A | 6/1985 | Ong et al. |
| 4,593,967 A | 6/1986 | Haugen |
| 4,675,731 A | 6/1987 | Takasu et al. |
| 4,679,076 A | 7/1987 | Vikterlof et al. |
| 4,726,046 A | 2/1988 | Nunan |
| 4,741,621 A | 5/1988 | Taft et al. |
| 4,825,393 A | 4/1989 | Nishiya |
| 4,853,777 A | 8/1989 | Hupp |
| 4,868,844 A | 9/1989 | Nunan |
| 5,080,100 A | 1/1992 | Trotel |
| 5,099,505 A | 3/1992 | Seppi et al. |
| 5,117,445 A | 5/1992 | Seppi et al. |
| 5,168,532 A | 12/1992 | Seppi et al. |
| 5,335,255 A | 8/1994 | Seppi et al. |
| 5,394,452 A * | 2/1995 | Swerdloff et al. ............ 378/65 |
| 5,438,991 A | 8/1995 | Yu et al. |
| 5,471,516 A | 11/1995 | Nunan |
| 5,537,452 A * | 7/1996 | Shepherd et al. ............ 378/65 |
| 5,692,507 A | 12/1997 | Seppi et al. |
| 5,751,781 A * | 5/1998 | Brown et al. ................. 378/65 |
| 5,956,382 A | 9/1999 | Wiener-Avnear et al. |

(Continued)

FOREIGN PATENT DOCUMENTS

| | | |
|---|---|---|
| DE | 42 23 488 A1 | 1/1994 |
| DE | 196 14 643 A1 | 10/1997 |
| EP | 0062941 B1 | 9/1984 |
| EP | 0205720 A1 | 12/1986 |
| EP | 0480035 B1 | 11/1994 |
| FR | 2 269 745 | 11/1975 |
| FR | 2 551 664 | 3/1985 |
| GB | 1 328 033 | 8/1973 |
| JP | 5[1993]-57028 | 3/1993 |
| WO | WO 85/03212 A1 | 8/1985 |

OTHER PUBLICATIONS

Ragan, "Correction for Distrotion in a Beam Outline Transfer Device in Radiotherapy CT–Based Simulation", Med. Phys. 20 (1), Jan./Feb. 1993, pp. 179–185.

Kuhn, "AIM Project A2003: COmputer VIsion in RAdiology (COVIRA)", Computer Methods and Programs in Biomedicine, 1994, Citation from Dissertation Abstracts, 1 page.

(Continued)

*Primary Examiner*—Edward J. Glick
*Assistant Examiner*—Allen C. Ho
(74) *Attorney, Agent, or Firm*—Blakely, Sokoloff, Taylor & Zafman LLP

(57) ABSTRACT

An apparatus including a first radiation source attached to a first gantry, at least one second radiation source, a second gantry that is rotatable; and an imager attached to an articulable end of the second gantry.

26 Claims, 10 Drawing Sheets

U.S. PATENT DOCUMENTS

| | | | | |
|---|---|---|---|---|
| 6,031,888 A | * | 2/2000 | Ivan et al. | 378/20 |
| 6,041,097 A | | 3/2000 | Roos et al. | |
| 6,104,778 A | | 8/2000 | Murad | |
| 6,104,780 A | * | 8/2000 | Hanover et al. | 378/92 |
| 6,144,875 A | | 11/2000 | Schweikard et al. | |
| 6,222,901 B1 | | 4/2001 | Meulenbrugge et al. | |
| 6,307,914 B1 | * | 10/2001 | Kunieda et al. | 378/65 |
| 6,325,537 B1 | * | 12/2001 | Watanabe | 378/197 |
| 6,381,302 B1 | | 4/2002 | Berestov | |
| 6,385,286 B1 | | 5/2002 | Fitchard et al. | |
| 6,429,578 B1 | * | 8/2002 | Danielsson et al. | 313/105 CM |
| 6,508,586 B2 | * | 1/2003 | Oota | 378/196 |
| 2001/0008271 A1 | | 7/2001 | Ikeda et al. | |
| 2003/0007601 A1 | | 1/2003 | Jaffray et al. | |

OTHER PUBLICATIONS

Keys, A CCTV–Microcomputer Biostereometric System for Use in Radiation Therapy (Topography, Medical Physics, Tissue Compensators), 1984, Citation from Energy Science and Technology, 1 page.

Kutcher et al., "Three dimensional radiation treatment planning", Citation from Engineering Index, 1988, 2 pages.

Redpath, et al., "Use of a Simulator and Treatment Planning Computer as a CT Scanner for Radiotherapy Planning", 1984, Citation from INSPEC., 1 page.

Elliott, "Interactive Image Segmentation for Radiation Treatment Planning", IBM Systems Journal, 1992, Citation from Medline (R) Database, 1 page.

Kushima et al., "New Development of Integrated CT Simulation System for Radiation Therapy Planning", Kobs J Med Sci., 1993, Citation from Medline (R) Database, 1 page.

Gademann et al., "Three–Dimensional Radiation Planning. Studies on Clinical Integration", Strahlenther Onkol, 1993, 1 page.

Ragan, "Correction for Distortion in a Beam Outline Transfer Device in Radkotherapy CT–based Simulation", Med Phys., 1993, 1 page.

Andrew et al., "A Video–Based Patient Contour Acquisition System for the Design of Radiotherapy Compensators", Med Phys., 1989, 1 page.

Reynolds, "An Algorithm for Three–Dimensional Visualization of Radiation Therapy Beams", Med Phys., 1988, 1 page.

Mohan, "Intersection of Shaped Radiation Beams with Arbitrary Image Sections", Comput Methods Programs Biomed, 1987, 1 page.

Brewsterfuauf, "Automatic Generation of Beam Apertures", Medical Physics, 1993, 1 page.

Hara et al., "Radiotherapeutic System", 00480035/EP–B1, Citation from World Patent, 1994 1 page.

Moore, "Radiation Image Generating System and Method", 1992020202/WO–A1, 1 page.

Seppi, "Computed Tomography Apparatus Using Image Intensifier Detector", 1992000567/WO–A1, 1 page.

Bova, "Dosimetric Technique for Stereotactic Radiosurgery", 1990014129/WO–A1, 1 page.

Kazufumi, "Radiation Treatment Device", 05057028 JP, 1 page.

Inamura, "CT Simulator For Radiotherapy", 63294839 JP, 1 page.

Moore, "Radiation Image Generating System and Method", Citation from US Patent, 2 pages.

Nishihara, "Therapeutic Apparatus", 2 pages.

Jaffray, "Cone–Beam CT: Application in Image Guided External Beam Radiotherapy and Brachytherapy", IEEE, 2000, 2 pages.

Ning et al., "An Image Intensifier–Based Volume Tomographic Angiography Imaging System: System Evaluation," SPIE, vol. 2432, pp. 280–290.

"Advanced Workstation for Irregular Field Simulation and Image Matching", Copyright 1999, MDS Nordion, 7 pages.

Balter, James M. et al., "Daily Targeting of Intrahepatic Tumors for Radiotherapy," Int. J. Radiation Oncology Biol. Phys., vol. 52, No. 1 (2002), pp. 266–271.

Swindell, William et al., "Computed Tomography With a Linear Accelerator With Radiotherapy Applications," Med. Phys., vol. 10, No. 4, Jul./Aug. 1983; pp. 416–420.

Mosleh–Shirazi, Mohammad Amin et al., "A Cone–Beam Megavoltage CT Scanner for Treatment Verification in Conformal Radiotherapy," Radiotherapy and Oncology, vol. 48 (1998), pp. 319–328.

Midgley, S. et al., "A Feasibility Study for Megavoltage Cone Beam CT Using A Commercial EPID," Phys. Med. Biol., vol. 43 (1998), pp. 155–169.

Ruchala, K.J. et al., "Megavoltage CT on a Tomotherapy System," Phys. Med. Biol., vol. 44 (1999), pp. 2597–2621.

Nakagawa, Keiichi, M.D. et al., "Megavoltage CT–Assisted Stereotactic Radiosurgery for Thoracic Tumors: Original Research in the Treatment of Thoracic Neoplasms," Int. J. Radiation Oncology Biol. Phys., vol. 48, No. 2, (2000), pp. 449–457.

Groh, B.A. et al., "A Performance Comparison of Flat–Panel Imager–Based MV and kV Conebeam CT," Med. Phys., vol. 29, No. 6, Jun. 2002, pp. 967–975.

Uematsu, Minoru et al., "Daily Positioning Accuracy of Frameless Stereotactic Radiation Therapy With a Fusion of Computed Tomography and Linear Accelerator (FOCAL) Unit: Evaluation of Z–Axis With a Z–Marker," Radiotherapy and Oncology, vol. 50, No. 3, Mar. 1999, pp. 337–339.

Uematsu, Minoru, M.D. et al., "A Dual Computed Tomography Linear Accelerator Unit for Stereotactic Radiation Therapy: A New Approach Without Cranially Fixated Stereotactic Frames," Int. J. Radiation Oncology Biol. Phys., vol. 35, No. 3 (1996), pp. 587–592.

Uematsu, Minoru, M.D. et al, "Intrafractional Tumor Position Stability During Computed Tomography (CT)–Guided Frameless Stereotactic Radiation Therapy for Lung or Liver Cancers With a Fusion of CT and Linear Accelerator (FOCAL) Unit," Int. J. Radiation Oncology Biol. Phys., vol. 48, No. 2 (2000), pp. 443–448.

Jaffray, David A., Ph.D. et al., "A Radiographic and Tomographic Imaging System Integrated Into a Medical Linear Accelerator for Localization of Bone and Soft–Tissue Targets," Int. J. Radiation Oncology Biol. Phys., vol. 45, No. 3 (1999), pp. 773–789.

Pisani, Laura, M.S. et al., "Setup Error in Radiotherapy: On–line Correction Using Electronic Kilovoltage and Megavoltage Radiographs," Int. J. Radiation Oncology Biol. Phys., vol. 47, No. 3 (2000), pp. 825–839.

Drake, D.G. et al, "Characterization of a Fluoroscopic Imaging System for kV and MV Radiography," Med. Phys., vol. 27, No. 5, May 2000, pp. 898–905.

Jaffray, D.A. and Siewerdsen, J.H., "Cone–Beam Computed Tomography with a Flat–Panel Imager: Initial Performance Characterization," Med. Phys., vol. 27, No. 6, Jun. 2000, 1311–1323.

Fahrig, R. and Holdsworth, D. W., "Three–Dimensional Computed Tomographic Reconstruction Using a C–Arm Mounted XRII: Image Based Correction of Gantry Motion Nonidealities," Med. Phys., vol. 27, No. 1, Jan. 2000, pp. 30–38.

Feldkamp, L.A. et al. "Practical Cone–Beam Algorithm," J. Opt. Soc. Am. A., vol. 1, No. 6, Jun. 1984; pp. 612–619.

Siewerdsen, Jeffrey H. and Jaffray, David A., "Optimization of X–Ray Imaging Geometry (With Specific Application to Flat–Panel Cone–Beam Computed Tomography)," Med. Phys., vol. 27, No. 8, Aug. 2000, pp. 1903–1914.

Siewerdsen, Jeffery H. and Jaffray, David A., "Cone–Beam Computed Tomography With a Flat–Panel Imager: Magnitude and Effects of X–Ray Scatter," Med. Phys., vol. 28, No. 2, Feb. 2001, pp. 220–231.

Cho, Paul S. et al., "Cone–Beam CT for Radiotherapy Applications," Phys. Med. Biol., vol. 40 (1995), pp. 1863–1883.

Masahiro et al., "Patient Beam Positioning System Using CT Images", Phys. Med. Biol., 1982, vol. 27, No. 2, pp. 301–305, printed in Great Britain.

* cited by examiner

RADIOTHERAPY APPARATUS EQUIPPED WITH AN ARTICULABLE GANTRY FOR POSITIONING AN IMAGING UNIT

FIELD OF THE INVENTION

The present invention pertains in general to oncology radiation therapy. In particular, the invention involves an X-ray and electron radiotherapy machine used in radiation treatment applications.

BACKGROUND OF THE INVENTION

The use of linear accelerators for the generation of either electron radiation or X-ray radiation is well known. After generating a stream of electrons, components in the radiotherapy machine can convert the electrons to X-rays, a flattening filter can broaden the X-ray beam, the beam can be shaped with a multileaf collimator, and a dose chamber can be arranged at the exit of an accelerator. A detector is mounted and is mechanically or electronically scanned synchronously with the mechanically or electronically scanned paraxial X-ray beam, providing continuous monitoring of alignment of the patient's anatomy. These systems typically provide either static fixed field radiation therapy or fully dynamic intensity modulated radiation therapy (IMRT) used by the medical community in the treatment of cancer.

One of the challenges inherent in radiotherapy treatment is the accurate positioning of the tumor in the radiation field. The main sources of the problem result from the fact that there is a natural motion of organs inside the body, which can range, for example, from approximately a millimeter in the case of the brain inside the skull, to several centimeters for the organs in the trunk above the diaphragm. Another factor relates to changes which occur in the tumor over time because of successful treatment. Over the course of treatment and as the tumor shrinks in volume, normal tissue which had been displaced returns to its original position within the treatment volume.

To accurately verify tumor positioning, detectors such as X-ray films or electronic X-ray imaging systems are commonly used in the radiation treatment diagnostic process. In the case of electronic imaging, the megavolt therapeutic X-rays emerging from the patient can be used to generate images. However, these methods at target location deliver images of low contrast and insufficient quality. As a result, imaging with megavoltage radiation is used primarily for verification, that is to confirm that the target volume has been radiated. These problems associated with utilizing high energy X-rays produced by a megavolt electron beam are the result of interacting with matter mostly due to Compton scattering, in which the probability of interactions is proportional to the electron density. Low energy X-rays typically have energies of about 125 peak kilovolts (kVp) or below, where a significant portion of the interactions with matter is photoelectric and the interactions are proportional to the cube of electron density. Low energy X-rays are more useful to provide accurate targeting or diagnostic information because tissue in the human body is typically of low density and as a result, the contrast achieved in low energy X-rays is far superior to that obtained with megavoltage X-rays. Therefore, distinctions of landmark features and the imaging of other features not perceptible with high energy X-rays are possible using kV energy. As a result, two separate imagers, each sensitive to an energy range, i.e. either the megavolt source or the kV source are used in treatment.

One method taught is to incorporate a low energy X-ray source inside the treatment head of the accelerator capable of positioning itself to be coincident with the high energy X-ray source. With this approach, a high energy X-ray target is modified to include a compact 125 kV electron gun to be mounted to a moveable flange at the base of the high energy source with the cathode of the gun operably coupled to the upstream end of a drift tube. By engaging an actuator, the electron gun can be provide target information for diagnostic imaging. An imager can be used that is sensitive to kV range radiation energies and positioned opposite the kV electron gun with the target volume in between. Therapeutic treatment can then be started or resumed by positioning the high-energy or megavolt electron beam trajectory to be in line with the target volume. A second imager is positioned opposing the megavolt source that is more sensitive to the radiation energy used in the therapeutic and verification procedure.

FIGS. 1A & 1B are illustrations of a radiotherapy clinical treatment machines to provide therapeutic and diagnostic radiation, each directed to a different imager. FIG. 1A is an illustration of the radiotherapy machine having a single diagnostic X-ray source directed to a single imager. The radiotherapy machine has a therapeutic radiation source directed to a therapeutic imager along a first axis and the diagnostic X-rays are directed to the second imager along an axis that is 90° from the first axis. This apparatus places the therapeutic radiation source capable of propagating radiation in the megavoltage (MV) energy range and the kilovoltage (kV) diagnostic radiation source on different support structures. Each radiation source has an imager opposing that is in line to the respective radiation source along an axis.

FIG. 1B is an illustration of the radiotherapy machine having dual diagnostic X-ray sources, each directed to a separate diagnostic imager. The radiotherapy machine has a therapeutic radiation source capable of propagating a therapeutic radiation beam along an axis to a therapeutic imager. Attached to support structures are two diagnostic radiation sources that can propagate diagnostic X-rays at off-angles from the therapeutic radiation axis. Each radiation source as an imager in line to receive the radiation. The entire structure of radiation sources and imagers can be pivoted together by a common base.

Cancer patients usually need to lie on their backs for radiation treatment and the patient's anatomy can shift markedly from supine to prone positions. In order to irradiate the target volume from different directions without turning the patient over, 360° rotation of the support structure holding the radiation source is needed. For convenience in setting up the patient, the isocenter around which the equipment rotates should not be too high above the floor. Adequate space must be provided between the isocenter and the radiation head for radiation technologist access to the patient and for rotation clearance around the patient. This leaves a quite limited amount of space for the various components such as the radiation shielding in the radiation head, and particularly for the magnet system. To a significant extent, the design challenge over the years has been to stay within this space, to reduce cost where possible, and while making major advances in the clinical utility of machines.

SUMMARY OF THE INVENTION

A radiotherapy clinical treatment machine can have a therapeutic radiation source on a first pivotable gantry. A second pivotable gantry can have a single imager mounted on an articulable end of the second gantry and a diagnostic radiation energy source can be mounted on a retractable opposing end of the second gantry. The first gantry and the second gantry may pivot on a common centerline. The imager can be a multiple-energy imaging unit which can be naturally in line with the diagnostic radiation source or the second gantry can pivot to place the multiple-energy imaging unit in line with the therapeutic radiation source. Pivoting the second gantry may require the diagnostic radiation source first be retracted to provide clearance where it rotates past the therapeutic radiation energy source.

This arrangement for positioning the multiple-energy imaging unit to be in line with either one of the radiation sources can provide improved imaging useful in directing the treatment beams used in radiation therapy. A first energy level in the kV range can radiate a target volume to provide diagnostic quality image information from the multiple-energy imaging unit. The diagnostic information can be used to better direct radiation at a second energy level in the MV range for therapeutic radiation of the target volume and from which verification information from the multiple-energy imaging unit can then be acquired. The second gantry can pivot, extend/retract, and/or articulate to receive diagnostic radiation or therapeutic radiation. The application of therapeutic radiation and diagnostic radiation can alternate in any combination to provide diagnostic imaging and verification imaging as a result of the degrees of freedom available to position the single multiple-energy imaging unit.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1A:
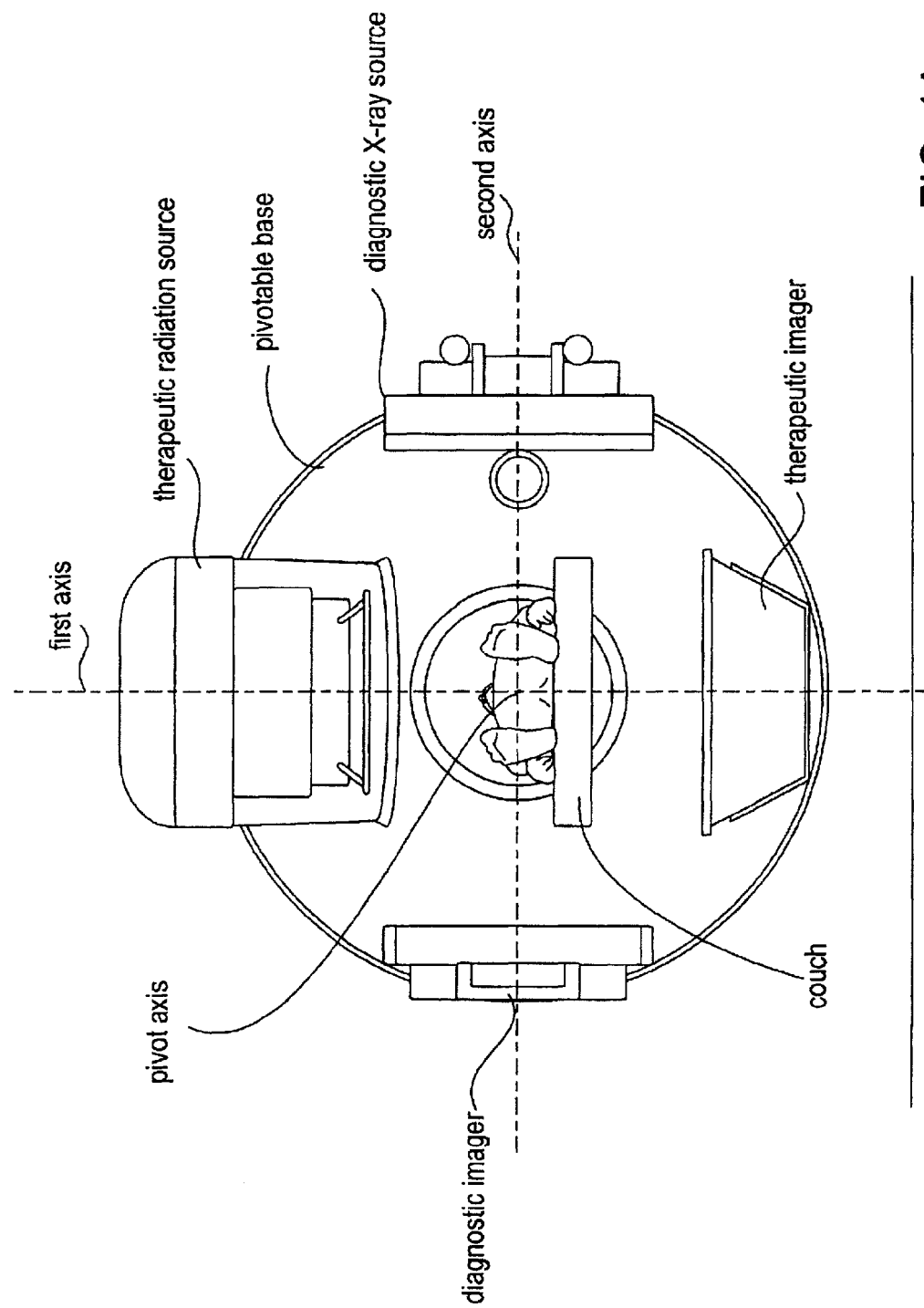
FIG. 1A is an illustration of the radiotherapy machine having a single diagnostic X-ray source directed to a single imager.
Figure 1B:
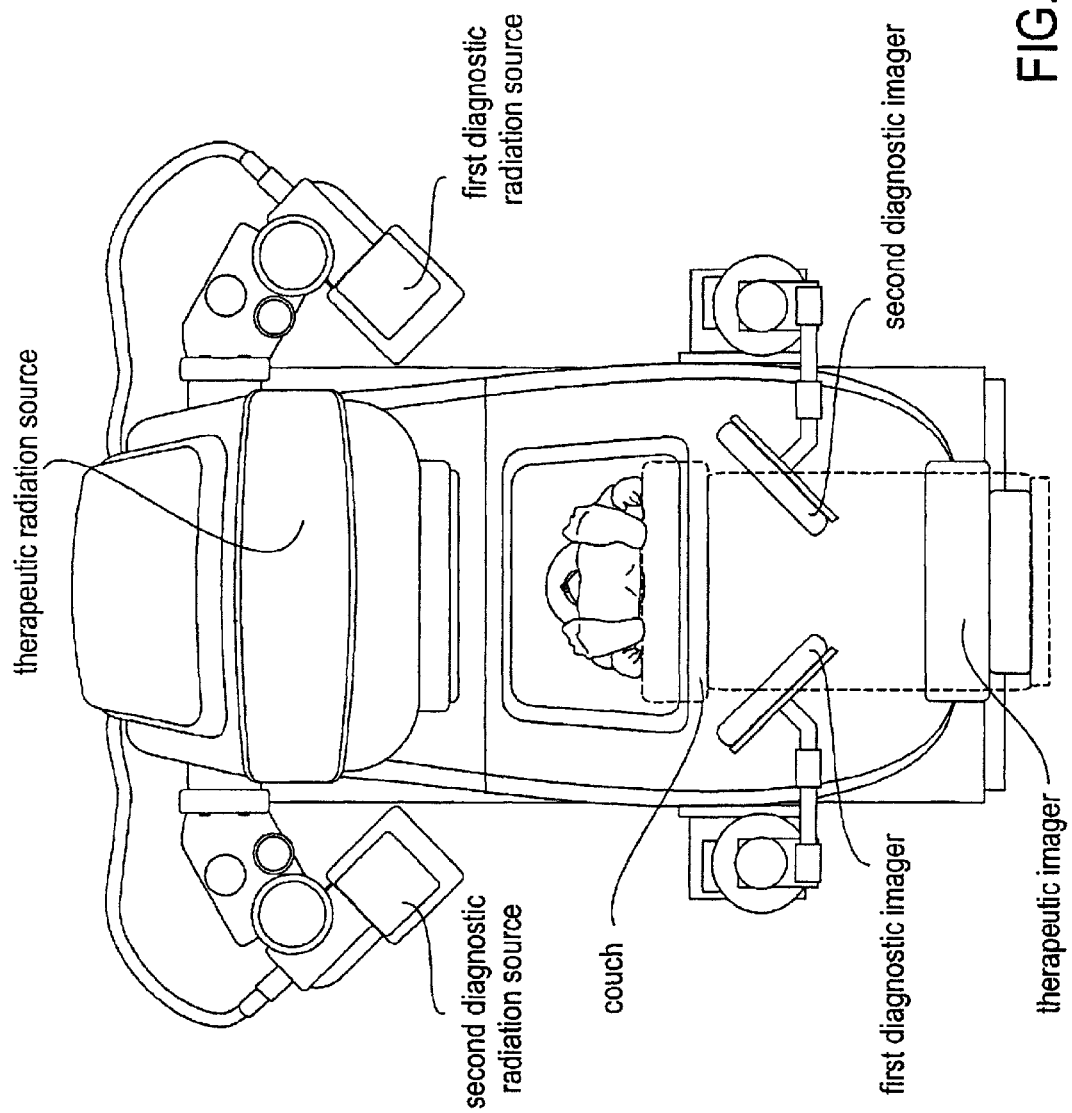
FIG. 1B is an illustration of the radiotherapy machine having dual diagnostic X-ray sources, each directed to a separate diagnostic imager.

A method and apparatus for a radiotherapy clinical treatment machine for positioning an imager to oppose one or more radiation sources is disclosed. For purposes of discussing the invention, it is to be understood that various terms are used by those knowledgeable in the art to describe apparatus, techniques, and approaches.

In the following description, for purposes of explanation, numerous specific details are set forth in order to provide a thorough understanding of the present invention. It will be evident, however, to one skilled in the art that the present invention may be practiced without these specific details. In some instances, well-known structures and devices are shown in gross form rather than in detail in order to avoid obscuring the present invention. These embodiments are described in sufficient detail to enable those skilled in the art to practice the invention, and it is to be understood that other embodiments may be utilized and that logical, mechanical, electrical, and other changes may be made without departing from the scope of the present invention.

In one embodiment, a method and apparatus is disclosed for an X-ray and electron radiotherapy clinical treatment machine. The apparatus and method can position and re-position a single imager to receive radiation from more than one radiation source. Imagers can generally provide high quality imaging from one radiation energy range and less quality imaging from other radiation energy ranges and such an imager can be incorporated into this invention. However, in this embodiment, the imager can be capable of receiving and displaying high quality imaging information from multiple energies (multiple-energy imaging unit). One of the energies can be a source of therapeutic energy and another a source of diagnostic X-rays, both of which can alternately activate the multiple-energy imaging unit for high quality verification imaging and high quality diagnostic imaging respectively. The radiotherapy machine can generate an electron beam, generally in the 4 to 25 megavolt (MV) range, to provide electrons or X-rays to a volume within a patient undergoing treatment, i.e. a target volume. The multiple-energy imaging unit can display radiographic information from the megavolt radiation sufficient to provide verification that the target volume is being radiated.

This single multiple-energy imager can also be optimized to work with energy in the kilovolt (kV) range. The multiple-energy imaging unit can receive X-rays in the kV range to provide more accurate diagnostic information on the size, shape, and location of the target volume. Repeated X-ray shots with kV energy that alternate with therapeutic radiation can reduce target error such as by directing a continuous adjustment of the beam shaping by a dynamic multileaf collimator and by providing targeting information to the therapeutic radiation source.

The diagnostic radiation source can be rotated about the target volume for CT single or multiple CT images using a fan x-ray beam, or by using a cone x-ray beam where volumetric information can be constructed. Also, if a partial data set is acquired from a limited number of images taken at specific angles around the target volume, enough information can be obtained with the help of previously acquired volumetric information to provide the 3D reconstruction of the anatomy of interest. As a result, imaging from the diagnostic X-rays can provide targeting information to accurately direct the therapeutic X-rays to the target volume from any angle while effectively excluding healthy tissue from injury. Furthermore, the diagnostic source can be operated either in a continuous or pulsed manner to provide a real time or quasi-real time fluoroscopic image of moving internal anatomy. This fluoroscopic image can be used to provide information to track the motion of anatomy being treated. Normal respiration or unwanted voluntary or involuntary patient movement may cause such motion. This motion tracking information can in turn be used to adjust treatment parameters or gate the treatment beam off and on such that the anatomy intended to be treated is always in the intended position within the treatment beam.

Figure 2A:
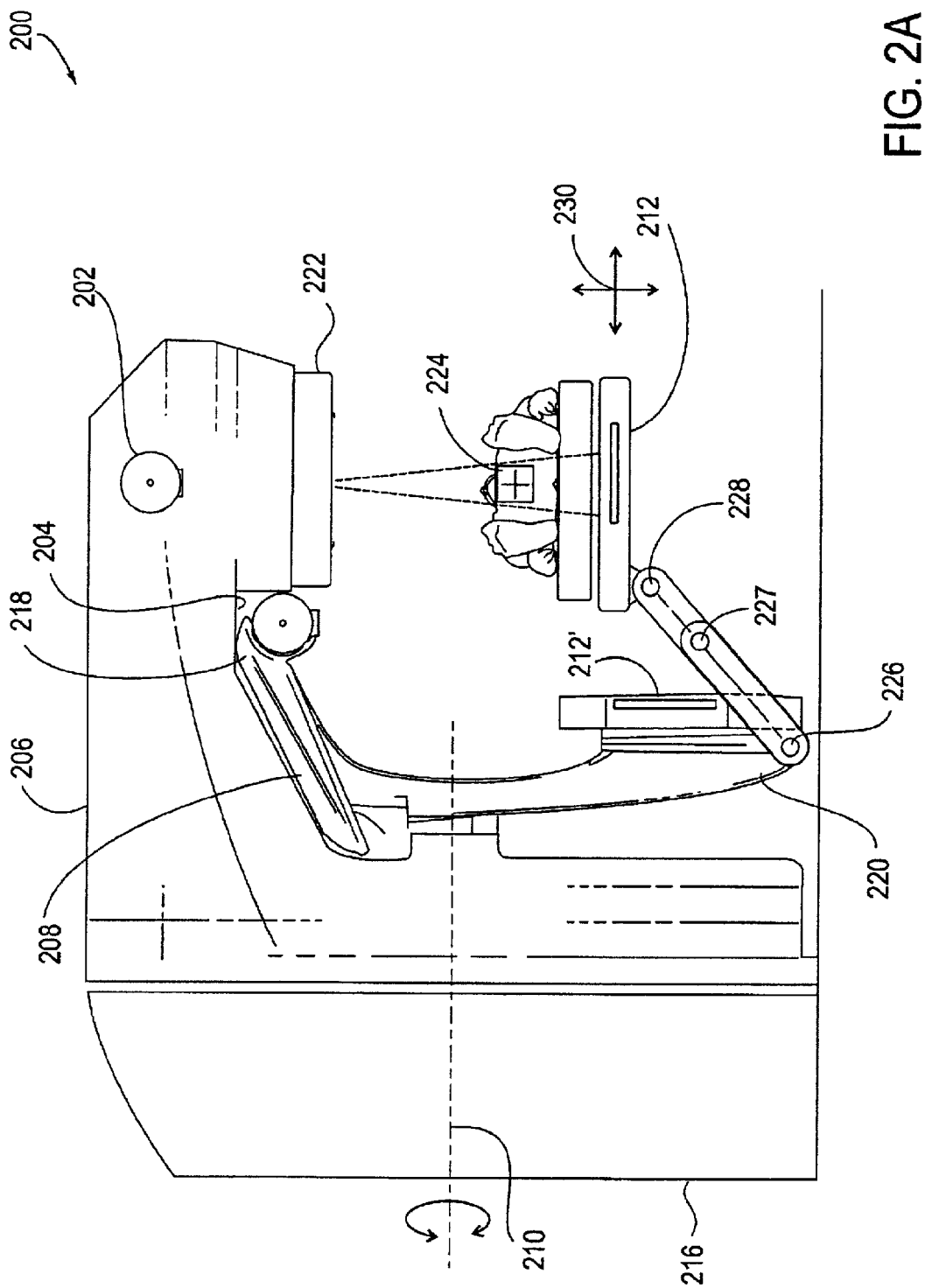
FIG. 2A is an illustration of a radiotherapy clinical treatment machine in one embodiment using a multiple-energy imaging unit.

FIG. 2A is an illustration of one embodiment of an imager positioning gantry on a radiotherapy clinical treatment machine where the imager can be a multiple-energy imaging unit. As shown in FIG. 2A, the radiotherapy clinical treatment machine 200 can have an imager positioning gantry to position the multiple-energy single imager to oppose one or more radiation sources. A therapeutic radiation source 202 and a diagnostic radiation source 204 can be positioned on separate arms (gantries), 206 and 208, where one arm (second gantry) 208 is nestled within the other (first gantry) 206, and with both arms 206 and 208 on a common pivot axis 210. The two arms 206 and 208 can pivot 210 independently and in addition, the inner arm (second gantry) 208 can extend and retract the diagnostic radiation source 204 for positioning and clearance. The therapeutic radiation source 202 can be positioned on the first arm (first gantry) 206 which can be pivotally attached to a vertical stand or base 216 to allow an effective 360° rotation of the therapeutic radiation source 202 about the target volume 224.

The imager can be a multiple-energy imaging unit and can be attached to the inner arm (second gantry) 208 at the end opposite from the diagnostic radiation source 204. The inner arm end 220 attached to the multiple-energy imaging unit 212 can articulate the multiple-energy imaging unit 212 into alignment with either radiation source 202 or 204. Attached to the second gantry 208, the multiple-energy imaging unit 212 is in natural alignment to receive radiation from an extended diagnostic radiation source 204. Fine adjustments to place the multiple-energy imaging unit into alignment with and at the proper distance from the radiation source 202 or 204 are also accomplished with the articulating portion of the second gantry 208. Alternately, the diagnostic radiation source 204 can be retracted for clearance so that the inner arm 220 can rotate and the multiple-energy imaging unit 212 articulate until the multiple-energy imaging unit 212 is in alignment to receive radiation from the other radiation source 202 or 204.

The first gantry 206 and the second gantry 208 can have a "C" shape (C-Arm) and the second gantry 208 can have a smaller radius of curvature and be nestled within the first gantry 206. The diagnostic X-ray source 204 can be mounted on one end 218 of the second gantry 208 and the multiple-energy imaging unit 212 to oppose on the other end 220. The radiation source end 218 of the second gantry 208 can extend or retract the diagnostic X-ray source 204 to provide clearance around the therapeutic radiation geometry (head) 222 on the first gantry 206. The diagnostic X-ray source 204 can also be extended and retracted, along with second gantry 208 rotation, to place the diagnostic X-ray source 204 in positions about the target volume 224. The articulating end 220 can be attached to an opposite end 220 of the second gantry C-arm 208 to hold and position the multiple-energy imaging unit 212. In one embodiment, the articulating end 220 can pivot at three points 226, 227, and 228 the multiple-energy imaging unit 212 along two independent axes 230 in a plane. The articulating end 220 can contain any number of pivot points from single plane pivots to ball joints having 360 degrees of rotation for positioning the multiple-energy imaging unit. The translatable 230 portion of the articulating joint can be a set of sliding mechanisms that include gears and motors which are well known to one skilled in the art. The result of such articulation can be to place the multiple-energy imaging unit in alignment with, and at a distance from, either of the radiation sources 202 and 204 with the target volume 224 positioned in between. Further, the articulating end 220 can retract to position the multiple-energy imaging unit 212 'into a stowed position.

Figure 2B:
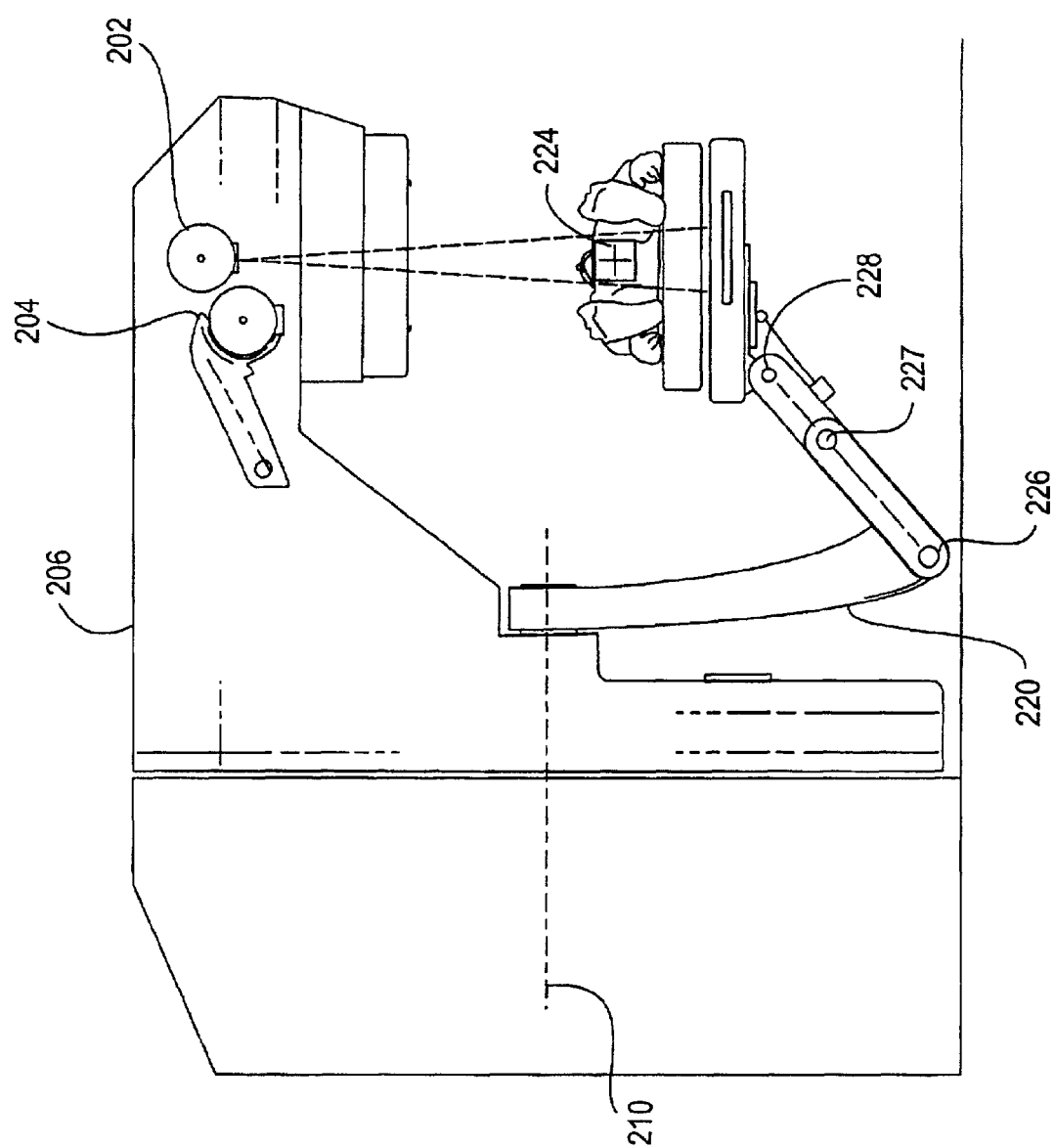
FIG. 2B is an illustration of an alternate embodiment of the radiotherapy clinical treatment machine using the multiple-energy imaging unit.

FIG. 2B is an illustration of an alternate embodiment of the radiotherapy clinical treatment machine using the multiple-energy imaging unit. As shown in FIG. 23, the therapeutic radiation source 202 and the diagnostic radiation source 204 can be positioned adjacent to each other and attached at the same end of the first gantry 206. The first gantry 206 can rotate about pivot axis 210 to position either the therapeutic radiation source 202 or the diagnostic radiation source 204 into alignment about the target volume 224. The second gantry, an inner arm, can be attached to the pivot axis 210 with an opposite end 220 attached to the articulating multiple-energy imaging unit 212. The multiple-energy imaging unit 212 can be rotated and articulated until alignment with either radiation source 202 or 204 is achieved, maintaining the target volume 224 in between.

Figure 3A:
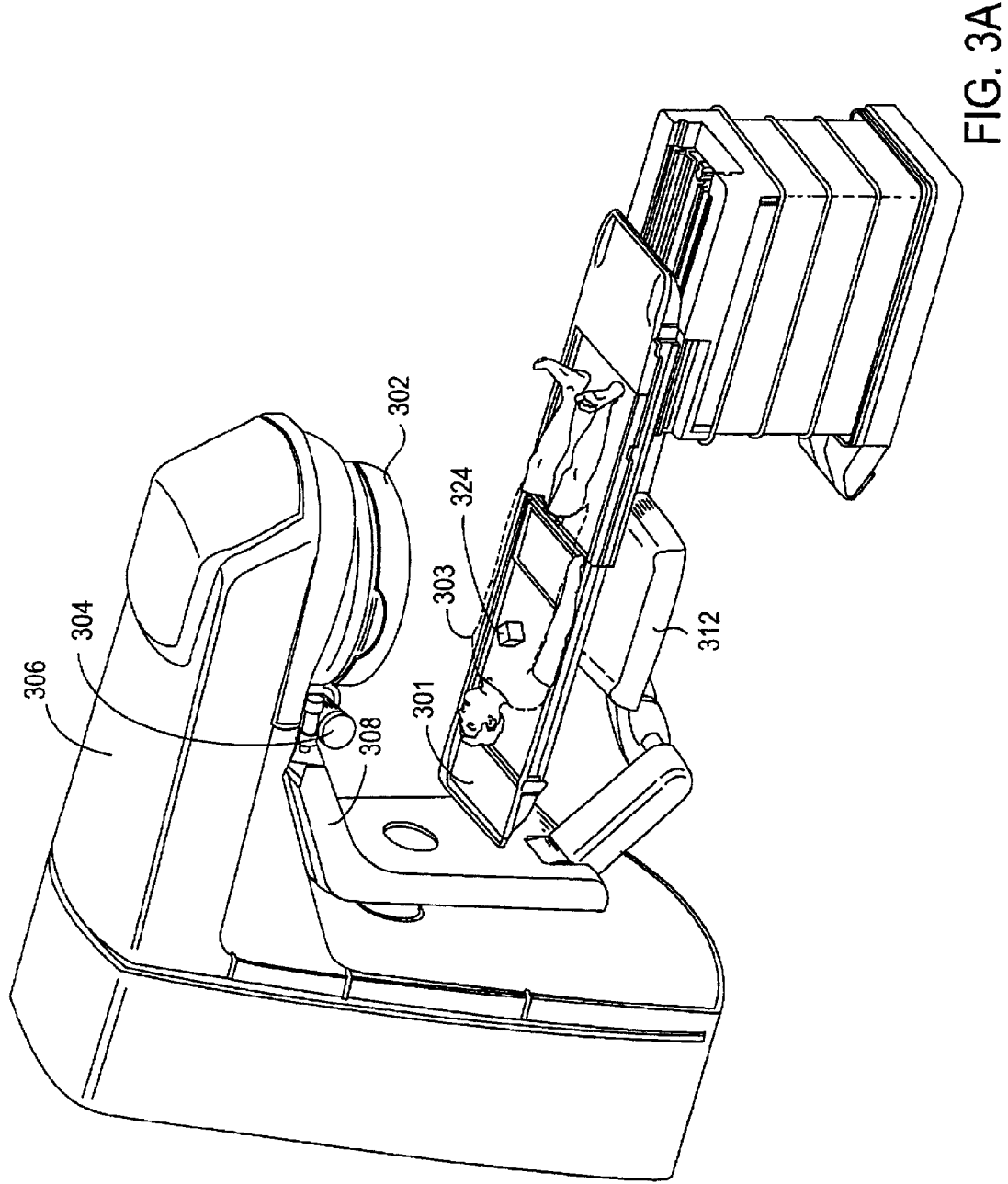
FIG. 3A is an illustration in one embodiment of the starting position for the radiotherapy clinical treatment machine.

FIGS. 3A–3E illustrate the operation of one embodiment of the radiographic clinical treatment machine. FIGS. 3B–3E retain the target volume 324 but have the patient outline 303 removed for clarity. FIG. 3A is an illustration of a starting position for the radiotherapy clinical treatment machine. A couch 301 can place a patient 303 in a starting position. The patient 303 can contain a volume within the body that constitutes the targeted volume 324. The first gantry 306 can be in an upright position, and the second gantry 308 can be upright with the diagnostic radiation source 304 in a retracted position. The multiple-energy imaging unit 312 can be unstowed and positioned beneath the couch 301.

Figure 3B:
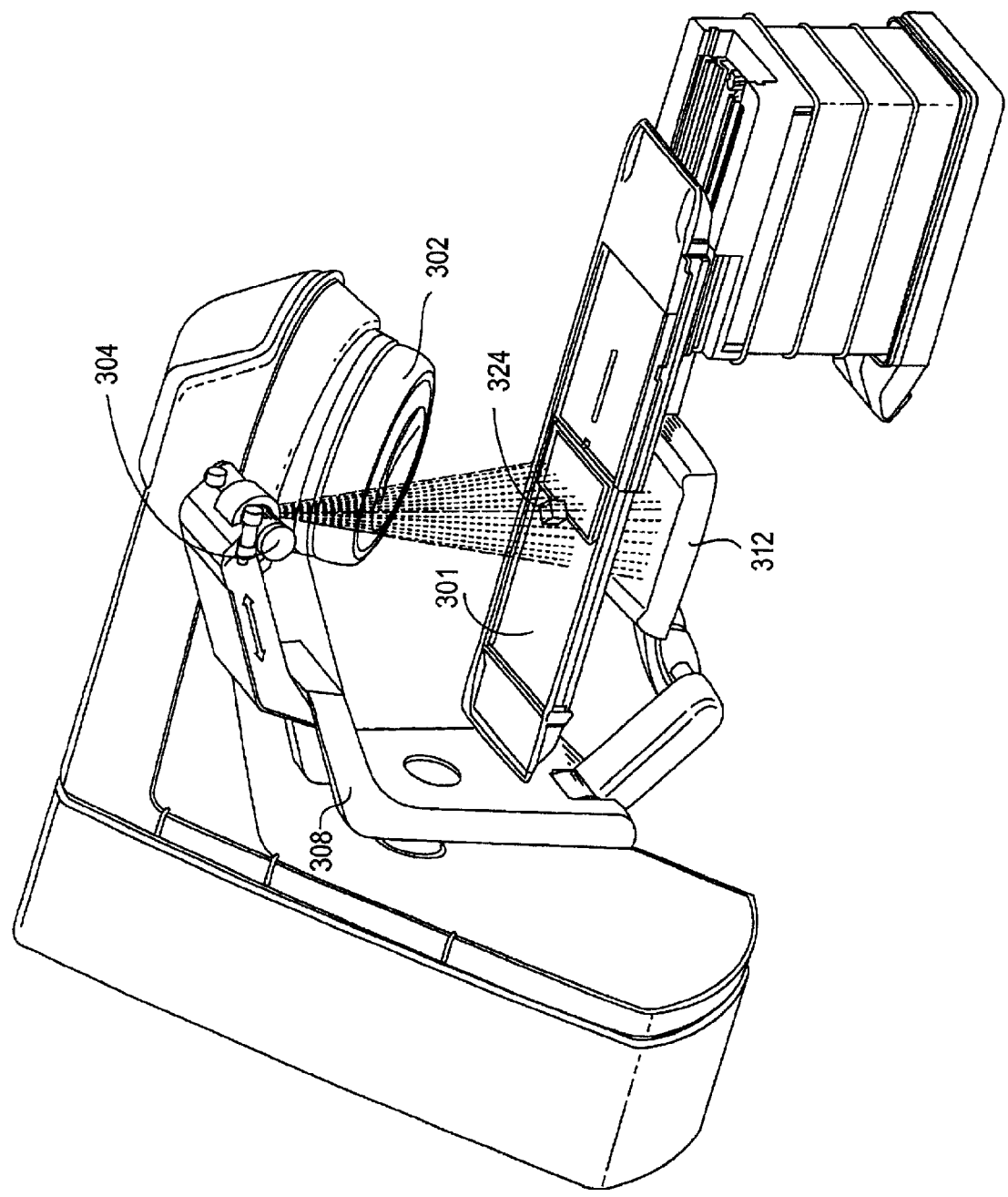
FIG. 3B is an illustration in one embodiment of a diagnostic radiation source in use.

FIG. 3B is an illustration of the diagnostic radiation source in use. The second gantry 308 can first rotate to provide clearance for the diagnostic radiation source 304 from the therapeutic radiation source 302. Once the diagnostic radiation source 304 is clear, the second gantry 308 can further rotate and extend the diagnostic radiation source 304 to be in alignment with the target volume 324 and maintain clearance between interfering geometries, i.e. 302 and 304. The multiple-energy imaging unit 312 can be further articulated and the couch 301 translated and raised or lowered until a proper alignment and distance is set relative to the target volume 324. When in position, the diagnostic radiation source 304 can direct an X-ray beam to the target volume 324 and then to the multiple-energy imaging unit 312.

Figure 3C:
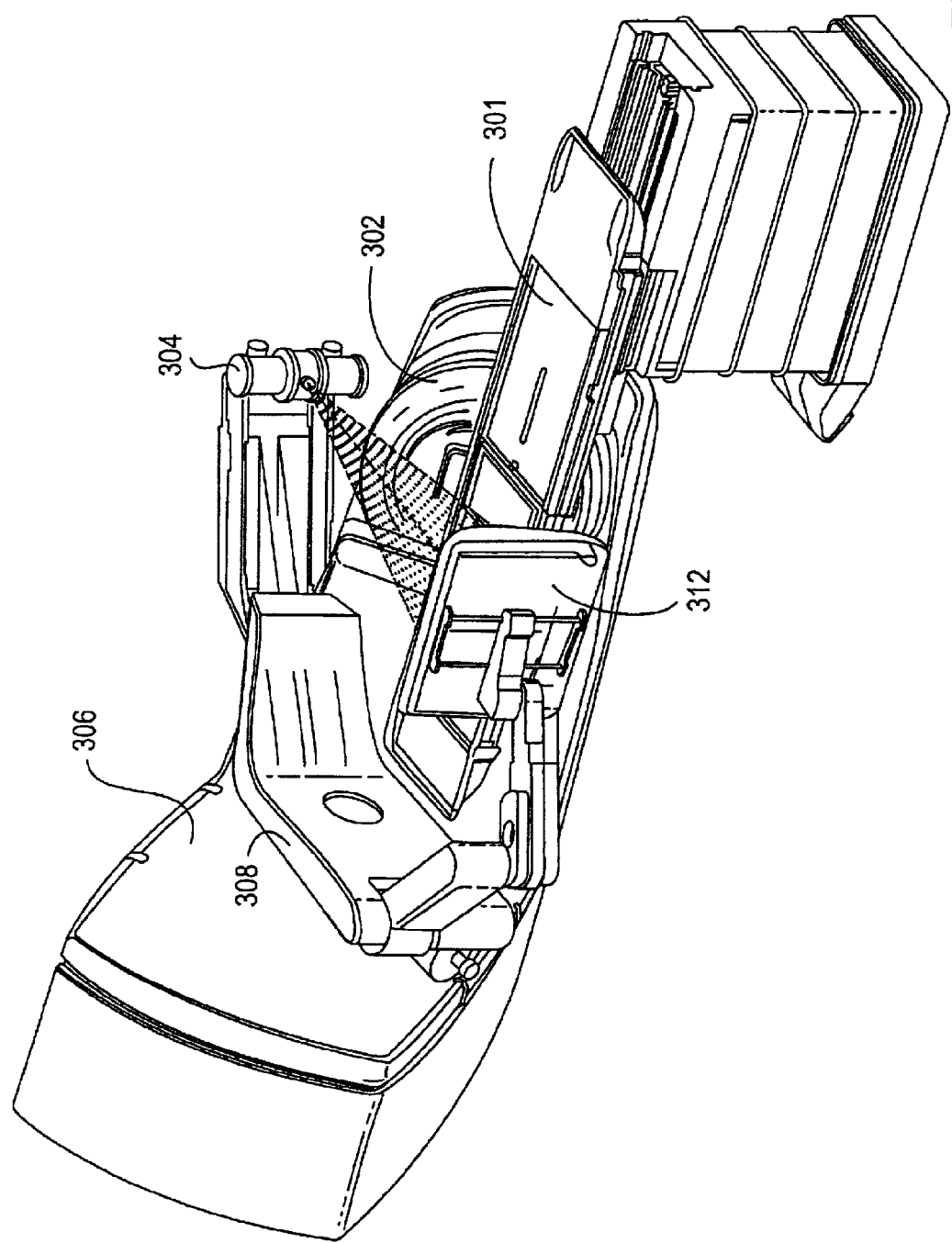
FIG. 3C is an illustration in one embodiment of the diagnostic radiation source providing multiple-slices of a target volume.

FIG. 3C is an illustration of the diagnostic radiation source providing another X-ray view of the target volume (not shown) at a new position. The diagnostic radiation source 304 and the multiple-energy imaging unit 312 can be rotated together by rotating any combination of either the first gantry 306 or the second gantry 308 to provide multiple X-ray views at different angles that can be assembled to generate 3-dimensional images of the target volume.

Figure 3D:
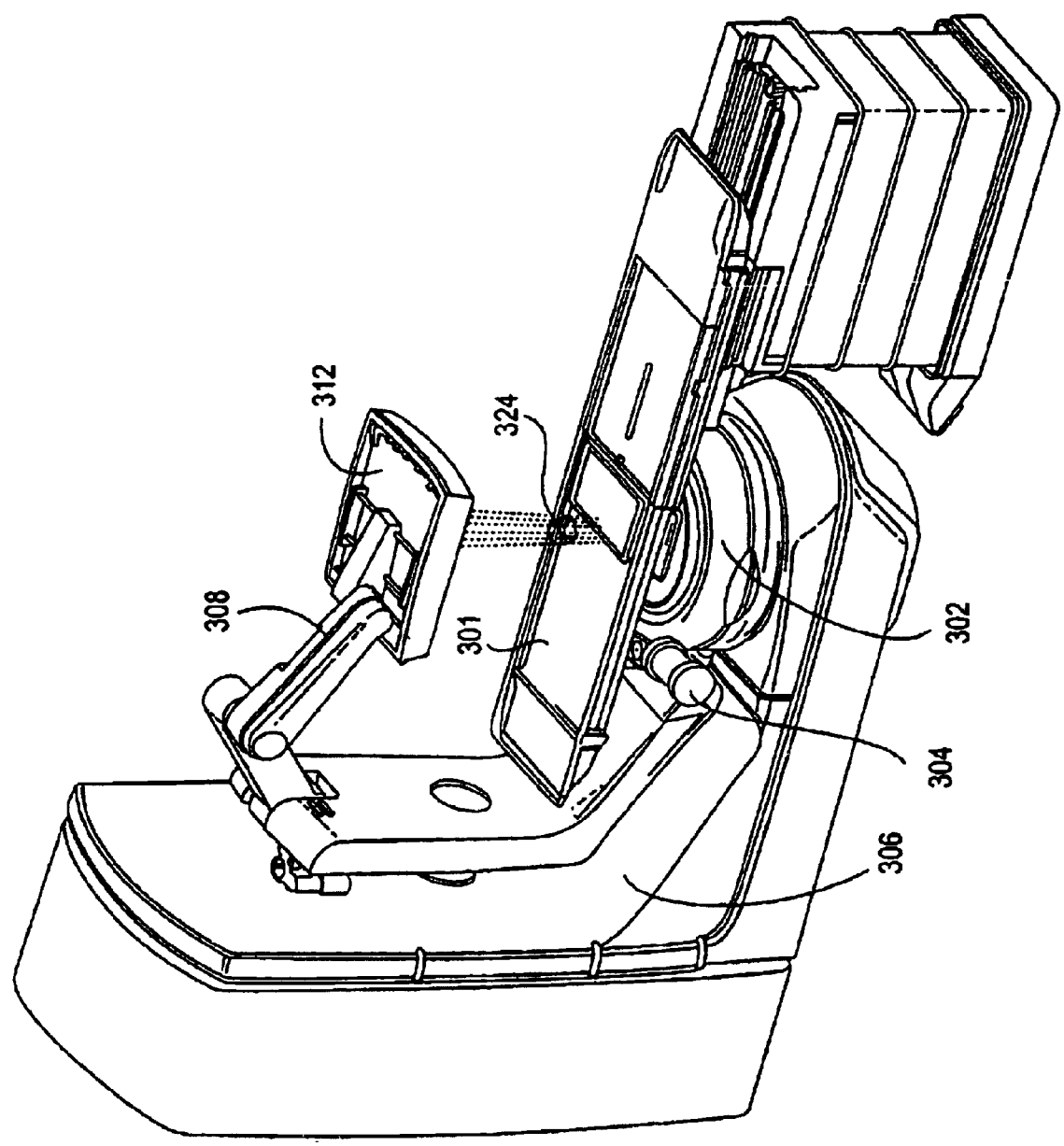
FIG. 3D is an illustration in one embodiment of a therapeutic radiation source providing radiation to the target volume.

FIG. 3D is an illustration of the therapeutic radiation source providing radiation to the target volume. After target volume definition has been provided by the diagnostic radiation step, the diagnostic radiation source 304 can be retracted for clearance and the second gantry 308 rotated until the multiple-energy imaging unit 312 opposes the therapeutic radiation source 302. The therapeutic radiation source 302 can be positioned to radiate the target volume 324 based on information gained from the diagnostic radiation step. At this point, the target volume 324 can receive a therapeutic dose of radiation and the multiple-energy imaging unit 312 can generate verification data from this same radiation.

Figure 3E:
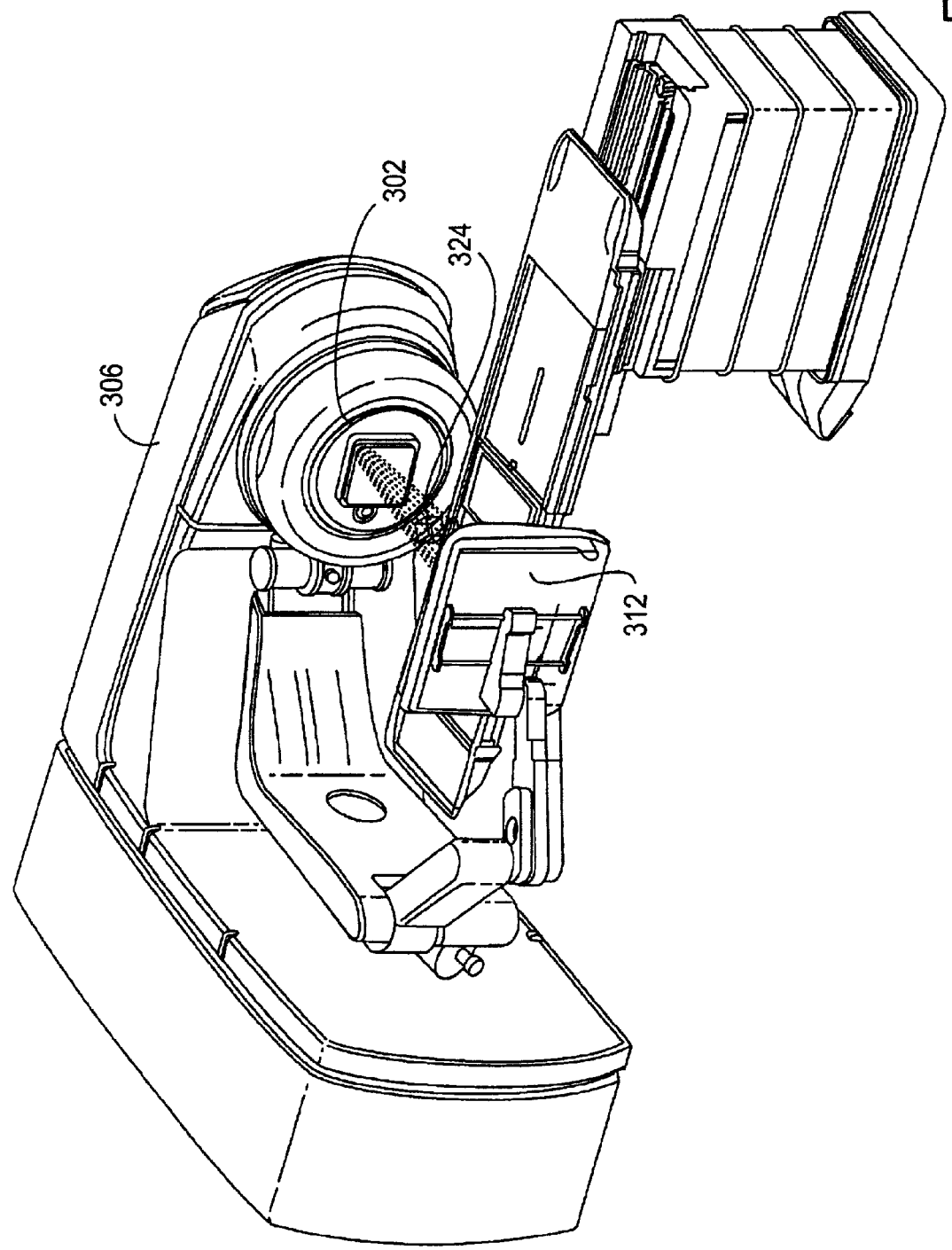
FIG. 3E is an illustration in one embodiment of the therapeutic radiation source rotated to a new position to provide radiation to the target volume.

FIG. 3E is an illustration of the therapeutic radiation source rotated to a new position to provide radiation to the target area 324. The first gantry 306 can be rotated, along with the multiple-energy imaging unit 312, to reposition the therapeutic radiation source 302 to radiate the target volume 324 from the new angle.

Figure 3F:
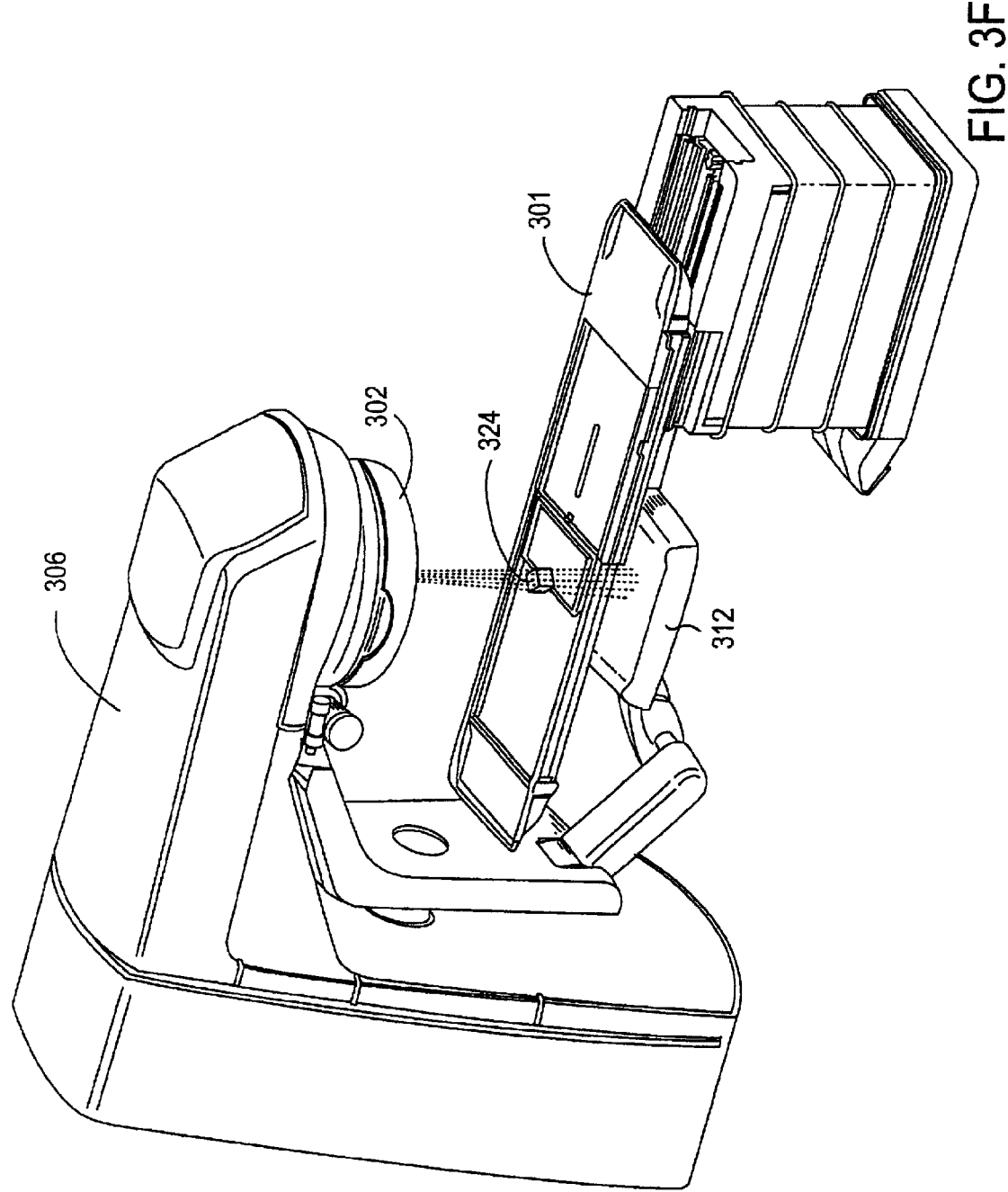
FIG. 3F is an illustration in one embodiment of another rotation of the first gantry and dose of therapeutic radiation applied to the target volume from another position.

FIG. 3F is an illustration of another rotation of the first gantry 306, and the multiple-energy imaging unit 312, to generate another dose of therapeutic radiation to the target volume 324 from yet another position. With each new position of the therapeutic radiation source 302, the multiple-energy imaging unit 312 and the couch 301 can be repositioned, new diagnostic imaging performed and another dose of therapeutic radiation initiated.

It is to be appreciated that, with this apparatus to position a single imager, it is possible to alternate therapeutic radiation with diagnostic radiation in several ways. In one method, the diagnostic radiation can provide imaging of a 2-dimensional nature. For therapeutic targeting, the therapeutic radiation source may be required to position itself at the same axis used by the diagnostic radiation source. In other methods, when multiple slices are taken or when using imaging data from a cone beam, a 3-dimensional construction is possible of the target area and therapeutic radiation can be targeted from any axis angle as a result.

In one embodiment, radiation at a first energy level can radiate a target volume along a first axis to provide diagnostic information to a multiple-energy imaging unit. Diagnostic information from the multiple-energy imaging unit can direct radiation at a second energy level along a second axis to provide therapeutic radiation to the target volume and verification information to the multiple-energy imaging unit. The first energy level can be in the kV energy range and the second energy level can be in the MV energy range. At any time during treatment, the first axis of radiation and the second axis of radiation can be the same or different. Diagnostic radiation and therapeutic radiation can alternate in any combination to provide diagnostic imaging and verification imaging by a single multiple-energy imaging unit for the overall radiation therapy of one or more target volumes.

The accuracy of diagnostic information can be improved by placing internal seeds to act as markers for the target volume. Placement of these markers can be accomplished by performing a needle biopsy. This is a commonly performed procedure normally required to gain tumor grading information needed to plan the therapy. These markers can provide higher contrast for the multiple-energy imaging unit for some tissues that might otherwise be difficult or impossible to discern. This can determine a more accurate location of the target volume and/or edges of the target volume. Marker data can be stored and recalled later to provide anatomical landmark definition to enhance position information on target volume during radiotherapy.

The multiple-energy imaging unit is a common portal imager capable of receiving radiation from the two radiation sources, each having a different energy level or range. One radiation source can provide energy in the megavolt range for treatment (therapeutic) and coarse target or verification information while the other radiation source can provide energy in the kilovolt range for determining a more precise location of target volumes (diagnostic) for periodically directing the megavolt energy source. The multiple-energy imaging unit can be a flat-panel amorphous silicon (a-Si) portal imaging device. A-Si flat-panel imagers can consist of a two-dimensional array of imaging pixels which are configured as photodiodes.

A multiple-energy imaging unit can display results from radiation from either a higher energy source, such as, for example, as used in therapeutic treatment or from radiation by a lower energy source such as, for example, as used in diagnostic purposes. A-Si imagers convert the optical signal from the overlaying phosphor, which acts together with a thin metal plate as an x-ray detector, to charge and store that charge on the pixel capacitance. To form an image, the charge on the pixels is read out line by line. Multiple-energy a-Si imagers may use a conversion screen design within the imager for multiple energy data unit collection from the two radiation sources. This specialized design can result in different spectral efficiency detection. One design is to use two or more conversion screen/a-Si detector layers, one on top of the other with a combined filter/grid design. Each screen layer will produce an image data unit for a particular radiation energy. One embodiment of a multiple-energy imaging unit, as discussed in U.S. patent application No. 10/013,199, titled "X-Ray Image Acquisition Apparatus", filed Nov. 2, 2001, and assigned with this application to a common owner at the date of filing, hereby incorporated by reference, may be used. Alternatively other imaging units may be used.

With this invention, the multiple-energy imaging unit can receive kV radiation that passes through the target volume. The multiple-energy imaging unit can then provide detailed location information for targeting by the therapeutic radiation source. During the application of therapeutic radiation, the multiple-energy imaging unit can be repositioned to receive megavoltage energy to provide verification information. A single imager can reduce the amount of space taken up in the treatment area by elements of a radiotherapy machine. In addition, a single imager can reduce cost and complexity for an overall IMRT system.

Thus a method and apparatus for a radiotherapy clinical treatment machine having a single imager attached to a pivotable and articulable gantry have been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. An apparatus comprising:
   a first therapeutic radiation source attached to a first gantry;
   at least one second radiation source;
   a second gantry that is rotatable, the second gantry is attached to the first gantry; and
   an imager attached to an articulable end of the second gantry.

2. The apparatus of claim 1, wherein at least one second radiation source is attached to the second gantry.

3. The apparatus of claim 1, wherein the first therapeutic radiation source to propagate therapeutic energy at a first energy level.

4. The apparatus of claim 1, wherein at least one second radiation source to propagate diagnostic energy at a second energy level.

5. The apparatus of claim 1, wherein the first gantry is rotatable.

6. The apparatus of claim 5, wherein the first gantry and the second gantry are rotatable about a common pivot axis.

7. The apparatus of claim 6, wherein the second gantry is nestled within the first gantry.

8. The apparatus of claim 1, wherein the imager is a multiple-energy imaging unit.

9. The apparatus of claim 1, wherein the articulable end comprises at least one pivot point between the second gantry and the imager.

10. The apparatus of claim 1, wherein the articulable end comprises a sliding mechanism capable of translating the imager in a plane.

11. The apparatus of claim 1, wherein the articulable end is capable of folding the imager against the second gantry.

12. An apparatus comprising:
a first radiation source attached to a first gantry;
at least one second radiation source, wherein the at least one second radiation source is attached to the first gantry;
a second gantry that is rotatable; and
an imager attached to an articulable end of the second gantry.

13. An apparatus comprising:
a first radiation source attached to a first gantry;
at least one second radiation source;
a second gantry that is rotatable, wherein the second gantry is capable of extending and retracting the second radiation source attached to the second gantry; and
an imager attached to an articulable end of the second gantry.

14. A method for applying radiation, comprising:
positioning a diagnostic X-ray source to be in alignment with a target volume;
positioning an imager at one of a plurality of distances from the target volume to receive radiation from the diagnostic X-ray source;
positioning a therapeutic radiation source to be in alignment with the target volume; and
re-positioning the imager to receive radiation from the therapeutic radiation source.

15. The method of claim 14, further comprising:
propagating diagnostic X-ray radiation from the diagnostic X-ray source toward the target volume;
receiving the diagnostic X-ray radiation on the imager after passing through the target volume;
positioning the therapeutic radiation source is based on results of the diagnostic X-ray radiation to the imager;
propagating the therapeutic radiation into the target volume;
receiving the therapeutic radiation by the imager after passing through the target volume; and
generating verification data by the imager from the therapeutic radiation.

16. The method of claim 15, further comprising generating multiple diagnostic X-ray radiation slices using a fan X-ray beam to provide a 3-dimensional reconstruction of the target volume.

17. The method of claim 15, further comprising generating a cone X-ray beam where volumetric information can be constructed.

18. The method of claim 15, wherein the diagnostic X-ray radiation can be operated continuously to provide real time a fluoroscopic image of moving internal anatomy.

19. The method of claim 15, wherein the diagnostic X-ray radiation can be operated in a pulsed manner to provide a quasi-real time fluoroscopic image of moving internal anatomy.

20. The method of claim 14, wherein the imager is a multiple-energy imaging unit.

21. The method of claim 14, further comprising placing an internal seed to act as a marker for the target volume.

22. A method for imaging radiation, comprising:
positioning a multiple-energy imaging unit normal to a first axis to receive radiation at a first energy level;
propagating radiation by a first radiation source at the first energy level along the first axis;
retracting the first radiation source and positioning a second radiation source along the first axis;
maintaining the multiple-energy imaging unit normal to the first axis to receive radiation by the second radiation source; and
propagating radiation by the second radiation source.

23. The method of claim 22, further comprising:
rotating the first radiation source until clear of the second radiation source;
extending the first radiation source to be in line with the multiple-energy imaging unit;
propagating radiation at a first energy level toward the multiple-energy imaging unit.

24. The method of claim 22, further comprising pivoting two arms independently, the first arm attached to the first radiation source for propagating at the first energy level, and the second arm attached to the second radiation source for propagating at the second energy level.

25. The method of claim 24, wherein the multiple-energy imaging unit is attached to the second arm.

26. An apparatus, comprising:
a therapeutic energy source attached to a first gantry;
a diagnostic X-ray energy source attached to a retractable end of a second gantry;
a multiple-energy imaging unit attached to an opposite articulable end of the second gantry;
the first gantry and the second gantry independently pivotable and attached at a common axis;
a patient couch capable of translation, wherein the result of such pivoting and translation is to place a target volume of a patient between the multiple-energy imaging unit aligned with the diagnostic energy source or the therapeutic energy source.

* * * * *